(12) United States Patent
Chen et al.

(10) Patent No.: US 8,911,968 B2
(45) Date of Patent: Dec. 16, 2014

(54) HIGH-YIELD PEPTIDE ANTIBIOTICS PRODUCING STRAIN, PREPARATION METHOD AND USE THEREOF

(75) Inventors: Yi Chen, Shanghai (CN); Shidong Liu, Shanghai (CN); Zhaoli Zhang, Shanghai (CN); Chunxia Wang, Shanghai (CN); Jing Kang, Shanghai (CN); Xiaoming Ji, Shanghai (CN)

(73) Assignee: Shanghai Techwell Biopharmaceutical Co., Ltd. (CN)

( * ) Notice: Subject to any disclaimer, the term of this patent is extended or adjusted under 35 U.S.C. 154(b) by 0 days.

(21) Appl. No.: 13/994,633

(22) PCT Filed: Dec. 15, 2011

(86) PCT No.: PCT/CN2011/084043
§ 371 (c)(1),
(2), (4) Date: Jul. 31, 2013

(87) PCT Pub. No.: WO2012/079521
PCT Pub. Date: Jun. 21, 2012

(65) Prior Publication Data
US 2014/0162314 A1  Jun. 12, 2014

(30) Foreign Application Priority Data
Dec. 15, 2010  (CN) .......................... 2010 1 0587865

(51) Int. Cl.
| C12P 21/04 | (2006.01) |
| C07K 7/54 | (2006.01) |
| C12R 1/645 | (2006.01) |
| C12N 15/01 | (2006.01) |
| C12N 1/14 | (2006.01) |
| C07K 7/56 | (2006.01) |

(52) U.S. Cl.
CPC . *C07K 7/54* (2013.01); *C12R 1/645* (2013.01); *C12N 15/01* (2013.01); *C12N 1/14* (2013.01); *C07K 7/56* (2013.01)
USPC . 435/71.1; 435/68.1; 435/254.1; 435/254.11; 435/256.8

(58) Field of Classification Search
None
See application file for complete search history.

(56) References Cited

FOREIGN PATENT DOCUMENTS

| CN | 1051757 A | 5/1991 |
| EP | 0462531 A2 | 5/1991 |
| WO | WO9947551 A1 | 9/1999 |

OTHER PUBLICATIONS

International Search Report for PCT/CN2011/084043 dated Mar. 22, 2012.
Kanda et al., Improvement of FR901379 Production by Mutant Selection and Medium Optimization, Journal of Bioscience and Bioengineering, vol. 107, No. 5, pp. 530-534, Apr. 22, 2009.

*Primary Examiner* — Jim Ketter
(74) *Attorney, Agent, or Firm* — McDermott Will & Emery LLP; Carey C. Jordan

(57) ABSTRACT

High-yield antibiotics producing strain, preparation method and use thereof are provided in the present invention. The high-yield strain is a mutagenized strain derived from *Colephoma empetri*, and deposited in CGMCC with the accession number of CGMCC 4129. The preparation method comprises the following steps: (a) mixing a seed liquid of *Colephoma empetri* of Accession No. FERM BP-2635 with nitrosoguanidine to obtain a mixture a; (b) mixing said mixture a with a wall-breaking enzyme to obtain protoplasts; (c) regenerating said protoplasts to obtain single colonies; and (d) culturing said single colonies to obtain said mutagenized strain. The obtained strain has stable genetic and producing property, produces little impurities in fermentation, and is suitable for industrialization.

8 Claims, No Drawings

HIGH-YIELD PEPTIDE ANTIBIOTICS PRODUCING STRAIN, PREPARATION METHOD AND USE THEREOF

This application is a U.S. national phase patent application of PCT/CN2011/084043 filed on Dec. 15, 2011, which published under WO2012079521, which claims priority to Chinese Patent Application No. 201010587865.4 filed on Dec. 15, 2010.

FIELD OF THE INVENTION

The present invention relates to the field of antibiotic production. In particular, the present invention relates to a strain producing peptide antibiotic with high yield, the preparation method and use thereof.

BACKGROUND OF THE INVENTION

In the past several decades, both the incidence and the types of fungus infection severely detrimental to human health were continuously increased, especially for the immunosuppressed patients. During this period, the clinical application of certain commonly used antifungal agents, such as amphotericin, imidazoles and triazoles, was restricted due to significant neurotoxicity, drug resistance, and the like. Echinocandins, as a kind of novel antifungal agents, are a group of natural products discovered in the 1970s. Structurally, the echinocandins have a similar cyclic polypeptide core but have different fatty acid side chains. Echinocandins can competitively inhibit the synthesis of β-D-glucan in fungal cell walls. The advantages of echinocandins are low toxicity, strong fungicidal activity, and as well as excellent pharmacokinetic properties.

Echinocandins family includes the following members: WF11899A, echinocandins, cilofungin, pneumocandins, aculeacins, and mulundocandin, with Micafungin, echinocandins and pneumocandins being actively investigated and currently applied clinically.

Micafungin is a water-soluble lipopeptide antifungal agent of echinocandins, which is obtained by chemically modifying the fermentation product from *Coleophoma empetri*. Micafungin has been developed by Fujisawa as a broad-spectrum antifungal agent. In an open study for patients with deep fungal infection (Candida or Aspergillus) conducted in Japan, 92% of the average efficiency can be reached after treating for about 22 days for each dose group. In a monocentre study conducted in the U.S. for 14 cases of cancer patients with candidemia, 50~150 mg of Micafungin is used in combination with other anti-fungus agents or without any other anti-fungus agent, and it was found that 11 cases were effective among 12 cases (92%). These kinds of drugs are superior to traditional antifungal agents, due to non-hemolytic toxicity and less drug interaction.

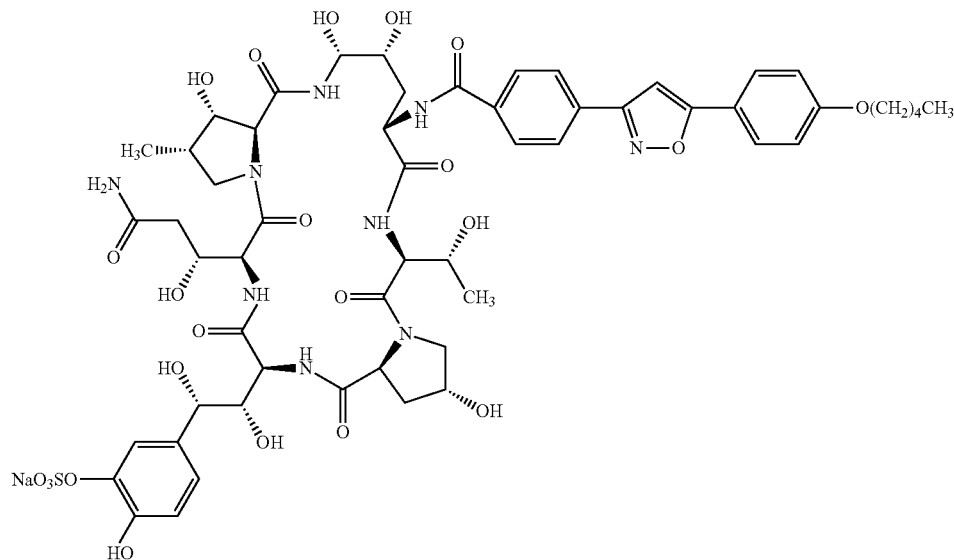

Structure of Micafungin

Coleophoma empetri can produce a class of natural antifungus agents, such as the compounds of Formula I, II, III.

The productivity of Coleophoma empetri (Accession No. FERM BP-2635) for the compound of Formula I is very low (merely 700 mg/L), therefore, the cost for industrialization will be very high.

General Formula I, II, III

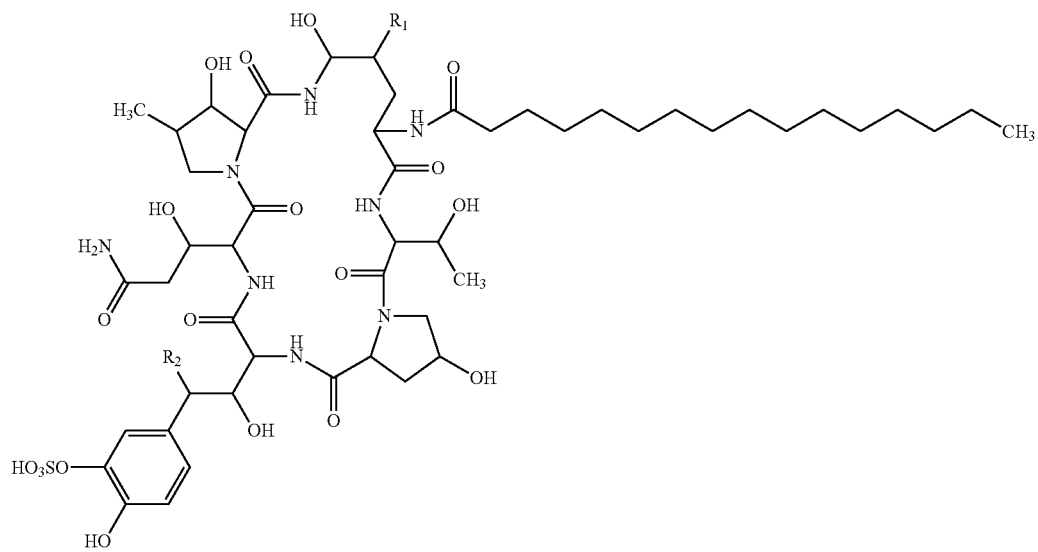

Formula I $R_1$=OH, $R_2$=OH
Formula II $R_1$=OH, $R_2$=H
Formula III $R_1$=H, $R_2$=H Accordingly, it is urgent to find a strain with stable genetic and high-yield properties which can produce more of the compound of Formula I for fulfilling the requirements of industrial production.

SUMMARY OF THE INVENTION

The object of the present invention is to provide a mutagenized strain of Coleophoma empetri.

Another object of the present invention is to provide a preparation method of said mutagenized strain.

Still another object of the present invention is to provide the use of said mutagenized strain.

In the first aspect of the present invention, a mutagenized strain of Coleophoma empetri is provided, which was deposited in the China General Microbiological Culture Collection Center with the Accession No. CGMCC 4129.

In the second aspect of the present invention, a preparation method of the mutagenized strain mentioned above is provided, comprising the following steps: (a) mixing a seed liquid of Coleophoma empetri of Accession No. FERM BP-2635 with nitrosoguanidine to obtain a mixture a; (b) mixing said mixture a with a wall-breaking enzyme to obtain protoplasts; (c) regenerating said protoplasts to obtain single colonies; and (d) culturing said single colonies to obtain the mutagenized strain said above.

In the third aspect of the present invention, the use of said mutagenized strain for producing the compound of formula I is provided:

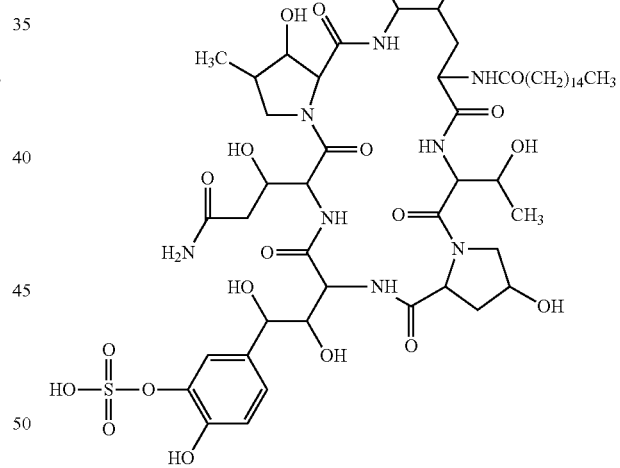

In the fourth aspect of the present invention, a preparation method of the compound of Formula I is provided, comprising the following step: culturing said mutagenized strain provided by the present method in a fermentation medium at a temperature of 15 to 35° C. to obtain the compound of formula I.

In the preparation method said above, said fermentation medium comprises the following components, based on the total volume of the fermentation medium: corn steep liquor 5-20 g/l, cottonseed meal 5-30 g/l, yeast extract 6-15 g/l, starch 10-80 g/l, glucose 5-20 g/l, inorganic salt 1.5-15 g/l, trace elements 10-50 g/l; said inorganic salt is selected from phosphate or sulfate or the combination thereof.

In the preparation method said above, the inoculation volume of said mutagenized strain provided by the invention is 4-10 v/v %, based on the total volume of the fermentation medium.

In the preparation method said above, the initial pH value of said fermentation medium is 5.5-6.5.

Summing up, the present invention provides a strain with stable genetic and high-yield properties which can produce more of the compound of Formula I for better fulfilling the requirements of industrial production.

DETAILED DESCRIPTION

The present inventors have surprisingly discovered that a high-yielding mutant strain (Accession No. CGMCC 4129) can be obtained by mutagenizing the strain *Coleophoma empetri* FERM BP-2635 with nitrosoguanidine (NTG), using lywallzyme to obtain protoplasts, and then screening the regenerated protoplasts. Said mutant strain can produce the compound of Formula I with high yield through fermentation. Thus, the inventors accomplished the present invention. FERM BP-2635 is available at the National Institute of Bioscience and Human Technology (formerly the "Fermentation Research Institute"), postal code 305-8566, 1-1-3, Higashi, Tsukuba-shi, Ibaraki, Japan, under the number of FERM BP-2635, which was deposited on Oct. 26, 1989.

New Strain

The present invention provides a new strain producing the compound of formula I. Taxonomically, said new strain belongs to *Coleophoma empetri* and has been deposited under terms in accordance with the Budapest Treaty with the China General Microbiological Culture Collection Center (China), at the Institute of Microbiology Chinese Academy of Sciences, Datun Road, Chaoyang District, Beijing 100101, China, with the Accession No. CGMCC 4129 on Aug. 31, 2010. All restrictions imposed by the depositor on the availability to the public of the deposited material will be irrevocably removed upon the granting of a patent in this application.

Preparation Method of the New Strain

The present invention provides a preparation method for the new strain with Accession No. CGMCC 4129, and said method can be carried out according to the following process: Starting strain; seed liquid; NTG mutagenesis treatment; removing cell wall by lywallzyme to obtain protoplasts; diluting and plating the protoplasts on dishes; picking single colony and seeding it on the slant; primary screening in shake flasks; selecting high-yielding strain; seeding the strain on the slant; secondary screening in shake flasks; selecting high-yielding strain, verifying in fermentation tank, and performing stability experiment; depositing strain.

In particular, the method provided in the present invention comprises the following steps: (a) mixing the seed liquid of *Coleophoma empetri* of Accession No. FERM BP-2635 with nitrosoguanidine to obtain the mixture a; (b) mixing said mixture a with the wall-breaking enzyme to obtain protoplasts; (c) regenerating said protoplasts to obtain single colonies; and (d) culturing said single colonies to obtain new strain.

In an example of the present invention, the new strain can be obtained by the following procedure: culturing the seed liquid of FERM BP-2635 (dry cell weight, DCW 5-30 g/l) for 1 to 3 days in shake flasks, adding an appropriate amount of NTG into the seed liquid, culturing for another 1 to 2 days, and then centrifuging the seed liquid, washing and resuspending the pellet and breaking the cell wall with lywallzyme (commercially available form Guangdong Microorganism institute) to obtain protoplasts. The diluted protoplasts were plated onto a hypertonic PDA (potato dextrose agar) plate and cultured to obtain recombinant cell single colonies. The single colonies said above are screened to obtain the mutagenized new strain.

Further, the present invention provides a method for producing the compound of formula I by fermenting the new strain obtained by mutagenesis.

In an example of the present invention, the method for obtaining the new strain by mutagenesis and fermenting the new strain to produce the compound of formula I is:

(1) Starting Strain: *Coleophoma empetri* FERM BP-2635

(2) Seed Culture of the Starting Strain

The deposited strain FERM BP-2635 in glycerol is thawed, seeded in a seed medium (loading amount 50 mL/250 mL), cultured on a shaker at 200-300 rpm at the temperature of 25-30° C. for 1 to 3 days till the dry weight of the mycelia reaches about 5-30 g/L.

The composition of the seed medium is: sucrose 10-20 g/L, yeast extract 4-10 g/L, soybean tryptone 10-20 g/L, $KH_2PO_4$ 1.5-2 g/L, $MgSO_4.7H_2O$ 0.4-1 g/L, trace elements 10-50 g/L, initial pH 5.3-6.0. The medium is sterilized at 121° C. for 20 mins.

Trace elements: $FeSO_4.7H_2O$ 10-20 g/L, $MnSO_4.H_2O$ 10-20 g/L, $ZnSO_4.7H_2O$ 2-10 g/L, $CaCl_2$ 0.7-2.0 g/L, $H_3BO_3$ 0.56-2.0 g/L, $CuCl_2.2H_2O$ 0.25-2.0 g/L, $(NH_4)_6Mo_7O_{24}.7H_2O$ 0.19-2.0 g/L, concentrated hydrochloric acid 500 ml/L.

(3) Separation of Single Colonies

Firstly, the seed liquid of the starting strain is subjected to the treatment of NTG mutagenesis, and then treated by lywallzyme to break cell wall. The resulting protoplasts are regenerated to obtain the mutant strain.

(4) Screening the Mutagenized Strain

The protoplasts are plated on a hypertonic PDA medium. The single colonies grown for 10 to 12 days are seeded on a slant medium for further culture. After 8 to 10 days, the seed medium is inoculated (loading amount 25 mL/250 mL) with the lawn grown on the slant medium, and cultured on a shaker at 280 rpm at the temperature of 25-30° C. for 6 to 10 days. The seed liquid is seeded into the fermentation medium (loading amount 25 mL/250 mL), and cultured on a shaker at 200 to 300 rpm at the temperature of 25-30° C. for 6 to 12 days. After the culture is completed, the fermentation liquid is extracted with methanol, and the content of the compound of formula I in the fermentation liquid is measured by high performance liquid chromatography.

The compositions of the medium involved can be found in Improvement of FR901379 production by mutant selection and medium optimization, Journal of Bioscience and Bioengineering Vol 107 No. 5, 530-534, 2009, Journal of antibiotics, Vol 45, No. 12, December 1992, 1867-1874.

Hypertonic PDA plate medium: potato 300 g/L, glucose 20 g/L, agar 15 g/L, sucrose 273.6 g/L, sterilized at 121° C. for 20 mins.

(5) Fermentation of the Mutagenized Strain

The relevant technical solutions have been reported in literature. For the details, please refer to Improvement of FR901379 production by mutant selection and medium optimization, Journal of Bioscience and Bioengineering VOL 107 No. 5, 530-534, 2009, Journal of antibiotics, Vol 45, No. 12, December 1992, 1867-1874.

The features of the present invention mentioned above, or the features mentioned in the examples, can be optionally combined. Any feature disclosed in the present specification can be used in combination with any other features, and each feature disclosed in the specification can be replaced with alternative feature which can serve an identical, equivalent, or similar purpose. Therefore, the features disclosed herein are only general exemplary examples of the equivalent or similar features, unless specifically indicated otherwise.

The main advantages of the present invention include:

1. A mutagenized new strain is obtained with stable high-yield and genetic properties.

2. The high genetic stability and less production of impurities of the new strain facilitate the product separation and purification during the production of the compound of formula I as well as the scale-up, thereby suitable for industrial production.

3. The yield of the compound of formula I can reach 1.5 g/L under optimized fermentation conditions.

The present invention will be further illustrated below with reference to specific examples. It should be understood that these examples are only to illustrate the present invention but not to limit the scope of the present invention. The experimental methods with no specific conditions described in the following examples are generally performed under conventional conditions or according to the manufacture's instruction. Unless indicated otherwise, all of the percentages, ratios, proportions, or parts are calculated by weight.

The unit of the weight to volume percentage used in the present invention is well known to those skilled in the art, for example, it refers to the weight of solute in a 100 milliliter of solution.

Unless otherwise defined, all the technical and scientific terms used in the present specification have the meanings as commonly understood by those skilled in the art. In addition, all of the methods and materials which are similar or equivalent with the contents disclosed herein can be applied in the present methods. The preferred methods and materials for carrying out the present methods described herein are only given as examples.

In the examples of the present invention, the conditions of the high performance liquid chromatography used to measure the content of the compound of formula I in the fermentation liquid are provided as follows: the content of the compound of formula I in the fermentation liquid is measured by the high performance liquid chromatography: chromatographic column: Calesil DOS-100 (4.6 mm×250 mm, 5 μm), mobile phase: acetonitrile: water=50:50 with 0.05 N of $NH_4H_2PO_4$, column temperature: 35° C., gradient elution, flow rate: 1.0 mL/min, injection volume: 5 μL, detection wavelength: 210 nm.

EXAMPLE 1

Obtaining the New Strain CGMCC 2933 by Mutagenesis

1. Mutagenesis

The deposited strain FERM BP-2635 in glycerol was thawed, seeded in a seed medium with an inoculation amount of 4% (loading amount 50 mL/250 mL), then cultured on a shaker at 280 rpm at 25° C. for 2 days, till the mycelia had a dry weight of about 5-30 g/L. The mutagen NTG was added to the seed liquid at a concentration of 10 μg/mL, and the seed liquid was cultured for another day. And then, 10 mL of the seed liquid containing NTG was taken, centrifuged at 5000 rpm for 10 minutes, and the obtained pellet was washed for two times with two volumes of 0.6 M NaCl for removing medium and NTG. The lethal rate for this process was 85-90%.

Seed medium: sucrose 10 g/L, yeast extract 5 g/L, soybean tryptone 10 g/L, $KH_2PO_4$ 1.5 g/L, $MgSO_4.7H_2O$ 0.4 g/L, trace elements 10 g/L, initial pH 5.3. The seed medium was sterilized at 121° C. for 20 mins.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

2. Protoplast Preparation and Single Colony Separation

To the washed mycelia, was added 10 mL of the enzyme mixture (in disodium hydrogen phosphate—citric acid buffer (pH 6.0) with 0.5 M NaCl), the enzyme mixture comprising 20 mg/mL of lywallzyme (2000 units/mg), 10 mg/ml of snail enzyme (5 units/mg), and 10 mg/ml of cellulose (15 units/mg). The resulting mixture was shaken at 80 rpm at 30° C. for 5 h for enzymolysis. The enzymolysis reaction mixture was filtered with cotton to remove mycelia and obtain a single-cell suspension comprising only protoplasts. One milliliter of this solution was taken and centrifuged at 14000 rpm for 10 mins. The precipitate was dissolved in 1 mL of disodium hydrogen phosphate—citric acid buffer (pH 6.0) comprising 0.5 M NaCl. This solution was then diluted serially into different concentrations, uniformly plated on a hypertonic PDA medium with 0.8 M sucrose, and cultured at 25° C. for 6 to 8 days to obtain about 6000 single colonies.

3. Screening Process of the High-Yield Strain CGMCC 4129

After culturing for 8 days, single colonies were picked and plated on slant media for further culture. After 8 days, the lawn with an area of 0.5 to 1.0 $cm^2$ was picked and seeded in a seed medium (loading volume 25 mL/250 mL) (4000 single colonies in total), cultured on a shaker at 280 rpm and 25° C. for 5 days. The seed liquid was seeded into a fermentation medium at an inoculation volume of 4% (loading volume 25 mL/250 mL), cultured on a shaker at 280 rpm and 25° C. for 10 days (5% starch was supplemented on day 6 of the culture).

After the culture was completed, the fermentation liquid was extracted with 50 ml of methanol, and the content of the compound of Formula I in the fermentation liquid was measured by high performance liquid chromatography. 5 high-yield strains were obtained in total, and the high-yield strain CGMCC 4129 was screened again to confirm that the yield of the compound of Formula I was 1.4 g/L.

EXAMPLE 2

Production of the Compound of Formula I by the New Strain CGMCC 4129

The new strain CGMCC 4129 obtained in Example 1 in the seed medium was seeded into a fermentation medium at an inoculation amount of 4%, and cultured in a 50 L fermentor at the temperature of 25° C. pH of the fermentation liquid was maintained at 6.5. After culturing for 10 days, the yield of the compound of formula I reached 1.5 g/L (5% starch was supplemented on day 6 of the culture).

Fermentation medium: corn steep liquor 20 g/l, cottonseed meal 10 g/l, yeast extract (commercially available form Oxiod) 8 g/l, starch 40 g/l, glucose 5-10 g/l, $KH_2PO_4$ 1.5 g/L, $MgSO_4.7H_2O$ 0.4 g/L, trace elements 10 ml/L, initial pH 5.3. Glucose was separately sterilized at 115° C. for 20 mins.

Trace elements: $FeSO_4.7H_2O$ 10 g/L, $MnSO_4.H_2O$ 10 g/L, $ZnSO_4.7H_2O$ 2 g/L, $CaCl_2$ 0.7 g/L, $H_3BO_3$ 0.56 g/L, $CuCl_2.2H_2O$ 0.25 g/L, $(NH_4)_6Mo_7O_{24}.7H_2O$ 0.19 g/L, concentrated hydrochloric acid 500 ml/L.

COMPARATIVE EXAMPLE

The capacity of the starting strain FERM BP-2635 for producing the compound of formula I was compared with that of the mutant strain CGMCC 4129 using the following methods:

The starting strain and the mutant strain were cultured using the culture method described in Example 2, respectively. After the culture was completed, the fermentation liquid was extracted using two volumes of methanol, and content of the compound of Formula I in the fermentation liquid was measured with high performance liquid chromatography. The results are shown in Table 1.

TABLE 1

| Strain No. | Yield of the compound of formula I (g · L$^{-1}$) |
|---|---|
| FERM BP-26357 | 0.07 |
| CGMCC 4129 | 1.5 |

The media used are listed as follows:

Screening medium: potato 300 g/L, glucose 20 g/L, agar 15 g/L, sucrose 273.6 g/L, sterilized at 121° C. for 20 mins.

Slant medium: potato 300 g/L, glucose 20 g/L, agar 15 g/L, sterilized at 121° C. for 20 mins.

Seed medium: sucrose 10 g/L, yeast extract 5 g/L, soybean tryptone 10 g/L, $KH_2PO_4$ 1.5 g/L, $MgSO_4 \cdot 7H_2O$ 0.4 g/L, trace elements 10 g/L, initial pH 5.3, sterilized at 121° C. for 20 mins.

Fermentation medium: corn steep liquor 20 g/l, cottonseed meal 10 g/l, yeast extract (commercially available form Oxiod) 8 g/l, starch 40 g/l, glucose 5-10 g/l, $KH_2PO_4$ 1.5 g/L, $MgSO_4 \cdot 7H_2O$ 0.4 g/L, trace elements 10 ml/L, initial pH 5.3. Glucose was separately sterilized at 115° C. for 20 mins.

Trace elements: $FeSO_4 \cdot 7H_2O$ 10 g/L, $MnSO_4 \cdot H_2O$ 10 g/L, $ZnSO_4 \cdot 7H_2O$ 2 g/L, $CaCl_2$ 0.7 g/L, $H_3BO_3$ 0.56 g/L, $CuCl_2 \cdot 2H_2O$ 0.25 g/L, $(NH_4)_6Mo_7O_{24} \cdot 7H_2O$ 0.19 g/L, concentrated hydrochloric acid 500 ml/L.

EXAMPLE 3

Stability of the New Strain CGMCC 4129

Subculture was carried out using the same medium and culture conditions described in Example 2. The result is shown in Table 2.

TABLE 2

| Passage number | F1 | F2 | F6 |
|---|---|---|---|
| Yield of the compound of formula I (g/L) | 1.5 | 1.3 | 1.6 |

The result shows that the new strain has an excellent stability.

The above description is merely the preferred examples of the present invention, and is not intended to limit the scope of the substantial technical contents of the present invention. The substantial technical contents of the present invention are broadly defined in the scope of the claims appended to the present application. Any technical entity or method accomplished by others should be deemed as falling into the scope of the claims of the present application if the entity or method is completely identical with that defined in the claims of the present application or an equivalent change or modification thereof.

The invention claimed is:

1. A mutagenized strain of *Coleophoma empetri*, deposited in China General Microbiological Culture Collection Center with the Accession No. CGMCC 4129.

2. A preparation method of the mutagenized strain according to claim 1, comprising the following steps:

(a) mixing a seed liquid of *Coleophoma empetri* of Accession No. FERM BP-2635 with nitrosoguanidine to obtain a mixture a;

(b) mixing said mixture a with a wall-breaking enzyme to obtain protoplasts;

(c) regenerating said protoplasts to obtain single colonies; and (d) culturing said single colonies to obtain the mutagenized strain according to claim 1.

3. The mutagenized strain according to claim 1 used for producing the compound of formula I:

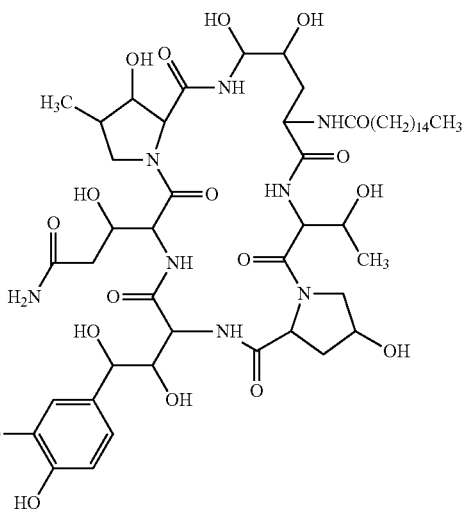

wherein the mutagenized strain is incubated in a fermentation medium.

4. A method for preparing the compound of Formula I:

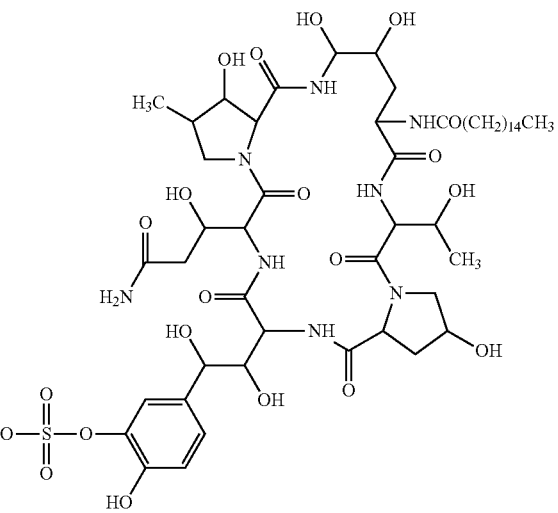

comprising the following step: culturing the mutagenized strain according to claim 1 in a fermentation medium at a temperature of 15 to 35° C. to obtain the compound of formula I.

5. The method according to claim 4, wherein said fermentation medium comprises the following components, based on the total volume of the fermentation medium: corn steep liquor 5-20 g/l, cottonseed meal 5-30 g/l, yeast extract 6-15 g/l, starch 10-80 g/l, glucose 5-20 g/l, inorganic salt 1.5-15 g/l, trace elements 10-50 g/l.

6. The method according to claim 5, wherein said inorganic salt is selected from phosphate or sulfate or the combination thereof.

7. The method according to claim 4, wherein the inoculation volume of said mutagenized strain according to claim 1 is 4-10 v/v %, based on the total volume of the fermentation medium.

8. The method according to claim 4, wherein the initial pH value of said fermentation medium is 5.5-6.5.

* * * * *